(12) United States Patent
Collombat et al.

(10) Patent No.: US 10,980,779 B2
(45) Date of Patent: Apr. 20, 2021

(54) GFI1 INHIBITORS FOR THE TREATMENT OF HYPERGLYCEMIA

(71) Applicants: INSERM (Institut National de la Santé et de la Recherche Médicale), Paris (FR); Université Nice Sophia Antipolis, Nice (FR); Centre National de la Recherche Scientifique (CNRS), Paris (FR)

(72) Inventors: Patrick Collombat, Nice (FR); Tiziana Napolitano, Nice (FR); Fabio Avolio, Nice (FR)

(73) Assignees: INSERM (INSTITUT NATIONAL DE LA SANTE ET DE LA RECHERCHE MEDICALE), Paris (FR); UNIVERSITE NICE SOPHIA ANTIPOLIS, Nice (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 16/496,761

(22) PCT Filed: Mar. 26, 2018

(86) PCT No.: PCT/EP2018/057680
§ 371 (c)(1),
(2) Date: Sep. 23, 2019

(87) PCT Pub. No.: WO2018/172570
PCT Pub. Date: Sep. 27, 2018

(65) Prior Publication Data
US 2020/0030292 A1  Jan. 30, 2020

(30) Foreign Application Priority Data

Mar. 24, 2017 (EP) .................................... 17305334

(51) Int. Cl.
*A61P 3/10* (2006.01)
*C12N 15/113* (2010.01)
*A61K 31/415* (2006.01)

(52) U.S. Cl.
CPC ............ *A61K 31/415* (2013.01); *A61P 3/10* (2018.01); *C12N 15/113* (2013.01); *C12N 2310/14* (2013.01)

(58) Field of Classification Search
CPC ..... A61P 3/10; C12N 15/113; C12N 2310/14; A61K 31/713
See application file for complete search history.

(56) References Cited

U.S. PATENT DOCUMENTS

2014/0296255 A1* 10/2014 Maes .................. A61K 31/135
  514/255.01
2015/0065434 A1   3/2015 Woster et al.

FOREIGN PATENT DOCUMENTS

EP   2 743 256 A1   6/2014

OTHER PUBLICATIONS

Zhang et al (Int J Clin Exp Med 2016;9(9):17739-17749) (Year: 2016).*
Vazzana et al (Thrombosis Research 129 (2012) 371-377) (Year: 2012).*
Maiques-Diaz et al (Mol. Cell. Oncol. 5(4):e1481813, 3 pages, 2018) (Year: 2018).*
Ishikawa et al (Mol Cancer Ther; 16(2) Feb. 2017) (Year: 2017).*
Furuya et al (J. Biol. Chem288(2): 16155-16166, May 31, 2013) (Year: 2013).*
Doiron (Diabetologia (2012) 55:719-728) (Year: 2012).*
Stazi et al.; "LSD1 Inhibitors: a patent review (2010-2015)"; Expert Opinion on Therapeutic Patents, vol. 26, No. 5, Mar. 28, 2016, pp. 565-580.

* cited by examiner

Primary Examiner — Richard A Schnizer
(74) Attorney, Agent, or Firm — W&C IP (57) ABSTRACT

The present invention relates to methods and pharmaceutical compositions useful for the treatment of hyperglycemia. Thorough multiple analyses, inventors demonstrated that Gfi1 is expressed in pancreatic acinar cells, starting from the first stages of pancreatic embryonic development. Furthermore, they observed that Gfi1 mRNA levels remain steady throughout embryonic development, while they significantly increase during the first days of life. They challenged conditional mutant mice with high fat diet for 5 months and monitored their weight and glycemia weekly. All the animals displayed a rapid increase in body mass as expected. While control mice rapidly developed a massive hyperglycemia, mutant mice remained normoglycemic throughout the entire experiment. A similar protection from induced diabetes was observed upon treatment with a high dose of Streptozotocin. Accordingly, the present invention relates to a method of treating hyperglycemia in a subject in need thereof comprising administering to the subject a therapeutically effective amount of an inhibitor of Gfi1.

1 Claim, 9 Drawing Sheets

GFI1 INHIBITORS FOR THE TREATMENT OF HYPERGLYCEMIA

FIELD OF THE INVENTION

The present invention relates to methods and pharmaceutical compositions useful for the treatment of hyperglycemia.

BACKGROUND OF THE INVENTION

The pancreas is an abdominal gland located behind the stomach and connected to the duodenum. It is divided into two functionally and morphologically distinct compartments: the exocrine and the endocrine tissues. The exocrine compartment (encompassing 98% of the total organ mass) represents a "factory" producing digestive enzymes that catalyze the breakdown of proteins, carbohydrates, and lipids. Pancreatic digestive enzymes are collected by intercalated ducts and are subsequently emptied into the duodenum (1). The endocrine compartment (representing less than 2% of the pancreatic tissue) is organized into highly vascularized and innervated cell clusters termed islets of Langerhans. These comprise five different hormone-secreting cell subtypes: $\alpha$-, $\beta$-, $\delta$-, $\epsilon$-, and PP-cells secreting respectively glucagon, insulin, somatostatin, ghrelin, and PP (pancreatic polypeptide—1-3). Insulin and glucagon act coordinately to maintain glycemic homeostasis by regulating the storage, metabolism, and neo-genesis of glucose. Insulin is released in response to increased blood glucose levels and acts by reducing glycemia through the induction of the storage and metabolism of glucose. Glucagon has the opposite function by promoting glucose release and/or neogenesis from glycogen, in case of hypoglycemia. Somatostatin and PP have been implicated in the regulation of other hormones and exocrine enzyme secretion (4-6). The function of ghrelin, synthesized and secreted by $\epsilon$-cells, is still unclear regarding glycemic homeostasis (7-9). Classical genetic approaches have revealed much about individual factors regulating pancreatic development (10), however, we have yet to understand the regulatory network underlying pancreas formation (11) and all the factors involved in this process. Some of these factors are well known and studied but increasing researches revealed new and unknown factors involved in pancreas development and maturation.

SUMMARY OF THE INVENTION

The present invention relates to methods and pharmaceutical compositions useful for the treatment of hyperglycemia. In particular, the present invention is defined by the claims.

DETAILED DESCRIPTION OF THE INVENTION

The first object of the present relates to a method of treating hyperglycemia in a subject in need thereof comprising administering to the subject a therapeutically effective amount of an inhibitor of Gfi1.

As used herein, the term "hyperglycemia has its general meaning in the art and refers to any elevated level of blood glucose compared to a basal level in a subject. "Basal level", as used herein, refers to a blood glucose level of a normal subject when fasting. Generally, hyperglycemia refers to blood glucose levels above about 100 mg/dl. In particular, hyperglycemia refers to blood glucose levels above about 110 mg/dl when fasting and above about 140 mg/dl two hours after having a meal.

According to the present invention, the inhibitor of Gfi1 is thus particularly suitable for reducing blood glucose levels and thus for achieving normoglycemia in the subject. As used herein, the expression "achieving normoglycemia" refers to the maintenance of blood glucose concentrations at the basal level.

In some embodiments, the subject suffers from diabetes. As used herein, the term "diabetes" has its general meaning in the art and refers to the chronic disease characterized by relative or absolute deficiency of insulin that results in hyperglycemia. The term "diabetes" is thus intended to include those individuals with hyperglycemia, including chronic hyperglycemia, hyperinsulinemia, impaired glucose homeostasis or tolerance, and insulin resistance.

In some embodiments, the subject suffers from Type 1 diabetes mellitus. As used herein, the term "Type 1 diabetes mellitus" or "T1D" has its general meaning in the art and refers to an autoimmune disorder than leads to destruction of the insulin producing beta cells of the pancreas leading to hyperglycemia.

In some embodiments, the subject suffers from type 2 diabetes. As used herein, the term "type 2 diabetes" or "non-insulin dependent diabetes mellitus (NIDDM)" has its general meaning in the art. Type 2 diabetes often occurs when levels of insulin are normal or even elevated and appears to result from the inability of tissues to respond appropriately to insulin. Most of the type 2 diabetics are obese. As used herein the term "obesity" refers to a condition characterized by an excess of body fat. The operational definition of obesity is based on the Body Mass Index (BMI), which is calculated as body weight per height in meter squared ($kg/m^2$). Obesity refers to a condition whereby an otherwise healthy subject has a BMI greater than or equal to 30 $kg/m^2$, or a condition whereby a subject with at least one co-morbidity has a BMI greater than or equal to 27 $kg/m^2$. An "obese subject" is an otherwise healthy subject with a BMI greater than or equal to 30 $kg/m^2$ or a subject with at least one co-morbidity with a BMI greater than or equal 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$. The increased risks associated with obesity may occur at a lower BMI in people of Asian descent. In Asian and Asian-Pacific countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. An "obese subject" in these countries refers to a subject with at least one obesity-induced or obesity-related co-morbidity that requires weight reduction or that would be improved by weight reduction, with a BMI greater than or equal to 25 $kg/m^2$. In these countries, a "subject at risk of obesity" is a person with a BMI of greater than 23 $kg/m^2$ to less than 25 $kg/m^2$.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "Gfi1" has its general meaning in the art and refers to the growth factor independent 1 transcriptional repressor (gene ID 2672). Gfi1 is also known as SCN2; GFI-1; GFI1A; ZNF163. This gene encodes a nuclear zinc finger protein that functions as a transcriptional repressor. This protein plays a role in diverse developmental contexts, including hematopoiesis and oncogenesis. Exemplary human nucleic acid and amino acid sequences are represented by the NCBI reference sequences NM_001127215.1 and NP_001120687.1 respectively.

Accordingly, an "inhibitor of Gfi1" refers to a compound, substance or composition that can inhibit the function of Gfi1. For example, the inhibitor can inhibit the expression or activity of Gfi1. Examples of Gfi1 inhibitors include but are not limited to polypeptides such as dominant-negative protein mutants, peptidomimetics, antibodies, ribozymes, antisense oligonucleotides, or other small organic molecules which specifically inhibit the activity or expression of Gfi1.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da. In a particular embodiment, the small molecule is T-3775440 as described in Ishikawa et al 2016. This molecule has the following structure in the art:

In some embodiments, the inhibitor is a short hairpin RNA (shRNA), a small interfering RNA (siRNA) or an antisense oligonucleotide which inhibits the expression of Gfi1. A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound. Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene. Anti-sense oligonucleotides include anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Antisense oligonucleotides, siRNAs, shRNAs of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically mast cells. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus;

and RNA virus such as a retrovirus. One can readily employ other vectors not named but known to the art.

In some embodiments, the inhibitor of Gif1 expression is an endonuclease. In the last few years, staggering advances in sequencing technologies have provided an unprecedentedly detailed overview of the multiple genetic aberrations in cancer. By considerably expanding the list of new potential oncogenes and tumor suppressor genes, these new data strongly emphasize the need of fast and reliable strategies to characterize the normal and pathological function of these genes and assess their role, in particular as driving factors during oncogenesis. As an alternative to more conventional approaches, such as cDNA overexpression or downregulation by RNA interference, the new technologies provide the means to recreate the actual mutations observed in cancer through direct manipulation of the genome. Indeed, natural and engineered nuclease enzymes have attracted considerable attention in the recent years. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR). Endonucleases for gene inactivation have come in various forms, which includes CRISPR/CRISPR associated (Cas) systems, mega nucleases (MN), zinc finger nucleases (ZFN), and transcription activator-like effector nucleases (TALEN). Endonucleases for use in the present invention are disclosed in WO 2010/079430, WO2011072246, WO2013045480, Mussolino C, et al (Curr Opin Biotechnol. 2012 October; 23(5):644-50) and Papaioannou I. et al (Expert Opinion on Biological Therapy, March 2012, Vol. 12, No. 3: 329-342).

In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences.

In some embodiment, the endonuclease is CRISPR-cas9 which is from Streptococcus pyogenes. The CRISPR/Cas9 system has been described in U.S. Pat. No. 8,697,359 B1 and US 2014/0068797. Originally an adaptive immune system in prokaryotes (Barrangou and Marraffini, 2014), CRISPR has been recently engineered into a new powerful tool for genome editing. It has already been successfully used to target important genes in many cell lines and organisms, including human (Mali et al., 2013, Science, Vol. 339: 823-826), bacteria (Fabre et al., 2014, PLoS Negl. Trop. Dis., Vol. 8:e2671.), zebrafish (Hwang et al., 2013, PLoS One, Vol. 8:e68708.), C. elegans (Hai et al., 2014 Cell Res. doi: 10.1038/cr.2014.11.), bacteria (Fabre et al., 2014, PLoS Negl. Trop. Dis., Vol. 8:e2671.), plants (Mali et al., 2013, Science, Vol. 339: 823-826), Xenopus tropicalis (Guo et al., 2014, Development, Vol. 141: 707-714.), yeast (DiCarlo et al., 2013, Nucleic Acids Res., Vol. 41: 4336-4343.), Drosophila (Gratz et al., 2014 Genetics, doi:10.1534/genetics.113.160713), monkeys (Niu et al., 2014, Cell, Vol. 156: 836-843.), rabbits (Yang et al., 2014, J. Mol. Cell Biol., Vol. 6: 97-99.), pigs (Hai et al., 2014, Cell Res. doi: 10.1038/cr.2014.11.), rats (Ma et al., 2014, Cell Res., Vol. 24: 122-125.) and mice (Mashiko et al., 2014, Dev. Growth Differ. Vol. 56: 122-129.). Several groups have now taken advantage of this method to introduce single point mutations (deletions or insertions) in a particular target gene, via a single gRNA. Using a pair of gRNA-directed Cas9 nucleases instead, it is also possible to induce large deletions or genomic rearrangements, such as inversions or translocations. A recent exciting development is the use of the dCas9 version of the CRISPR/Cas9 system to target protein domains for transcriptional regulation, epigenetic modification, and microscopic visualization of specific genome loci.

In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

In some embodiments, the inhibitor is an intrabody having specificity for Gfi1. As used herein, the term "intrabody" generally refer to an intracellular antibody or antibody fragment. Antibodies, in particular single chain variable antibody fragments (scFv), can be modified for intracellular localization. Such modification may entail for example, the fusion to a stable intracellular protein, such as, e.g., maltose binding protein, or the addition of intracellular trafficking/localization peptide sequences, such as, e.g., the endoplasmic reticulum retention. In some embodiments, the intrabody is a single domain antibody. In some embodiments, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

As used herein the terms "administering" or "administration" refer to the act of injecting or otherwise physically delivering a substance as it exists outside the body (e.g., an inhibitor of Gif1) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

By a "therapeutically effective amount" of the inhibitor as above described is meant a sufficient amount to provide a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the inhibitor is administered to the subject in the form of a pharmaceutical composition. Typically, the inhibitor may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In some embodiments, the inhibitor of the present invention is administered to the subject in combination with another diabetes medications. Exemplary diabetes medications include sulfonylureas, meglitinides, biguanides, thiazolidinediones, alpha-glucosidase inhibitors, or DPP-4 inhibitors. Sulfonylureas stimulate the beta cells of the pancreas to release more insulin. Chlorpropamide (Diabinese) is the only first-generation sulfonylurea still in use today. The second generation sulfonylureas are used in smaller doses than the first-generation drugs. There are three second-generation drugs: glipizide (Glucotrol and Glucotrol XL), glyburide (Micronase, Glynase, and Diabeta), and glimepiride (Amaryl). Meglitinides are drugs that also stimulate the beta cells to release insulin. Repaglinide (Prandin) and nateglinide (Starlix) are meglitinides. Metformin (Glucophage) is a biguanide. Biguanides lower blood glucose levels primarily by decreasing the amount of glucose produced by the liver. Rosiglitazone (Avandia) and pioglitazone (ACTOS) are in a group of drugs called thiazolidinediones. These drugs help insulin work better in the muscle and fat and also reduce glucose production in the liver. DPP-4 inhibitors help improve AIC without causing hypoglycemia. They work by preventing the breakdown of a naturally occurring compound in the body, GLP-1. GLP-1 reduces blood glucose levels in the body, but is broken down very quickly so it does not work well when injected as a drug itself. By interfering in the process that breaks down GLP-1, DPP-4 inhibitors allow it to remain active in the body longer, lowering blood glucose levels only when they are elevated. Sitagliptin (JANUVIA) and saxagliptin (ONGLYZA) are the two DPP-4 inhibitors currently on the market.

A further object of the present invention relates to a method of screening a drug suitable for the treatment of hyperglycemia comprising i) providing a test compound and ii) determining the ability of said test compound to inhibit the expression or activity of Gfi1.

Any biological assay well known in the art could be suitable for determining the ability of the test compound to inhibit the activity or expression of Gfi1. In some embodiments, the assay first comprises determining the ability of the test compound to bind to Gfi1. In some embodiments, a population of pancreatic cells (acinar, ductal or endocrine) is then contacted and activated so as to determine the ability of the test compound to inhibit the activity or expression of Gfi1. In particular, the effect triggered by the test compound is determined relative to that of a population of immune cells incubated in parallel in the absence of the test compound or in the presence of a control agent either of which is analogous to a negative control condition. The term "control substance", "control agent", or "control compound" as used herein refers a molecule that is inert or has no activity relating to an ability to modulate a biological activity or expression. It is to be understood that test compounds capable of inhibiting the activity or expression of Gfi1, as determined using in vitro methods described herein, are likely to exhibit similar modulatory capacity in applications in vivo. In vivo assays are well known in the art and typically include those described in the EXAMLE. Typically, the test compound is selected from the group consisting of peptides, petptidomimetics, small organic molecules, antibodies (e.g. intraantibodies), aptamers or nucleic acids. For example the test compound according to the invention may be selected from a library of compounds previously synthesised, or a library of compounds for which the structure is determined in a database, or from a library of compounds that have been synthesised de novo. In some embodiments, the test compound may be selected form small organic molecules.

The invention will be further illustrated by the following figures and examples. However, these examples and figures should not be interpreted in any way as limiting the scope of the present invention.

FIGURES

FIG. 7: Intraperitoneal glucose tolerance test on 3 months old mice (A) and 6.5 months old mice (B). Intraperitoneal insulin tolerance test on 3 months old mice (C) and 6.5 months old mice (D).

FIG. 8: Weight and basal glycemia monitoring of control and Gfi1 mutant mice subjected to high fat diet (A-B). Glucose tolerance test (C) and insulin tolerance test (D) performed on mice of the indicated genotypes following exposure to high fat diet for 5 months.

EXAMPLE

Figure 1:
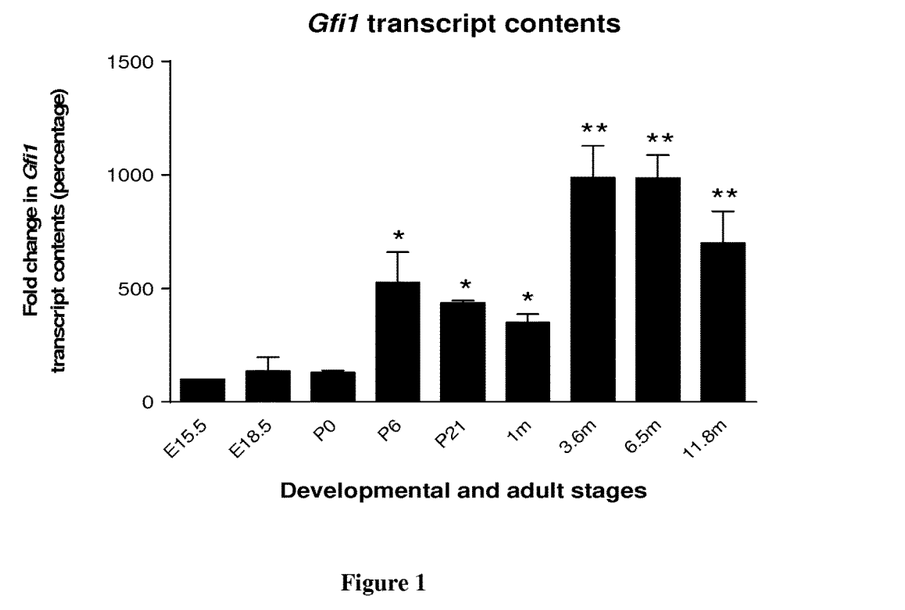
FIG. 1: qRT-PCR quantification of Gfi1 expression in mouse pancreas from E15.5 (embryonic day 15.5) to 11.8 months of age.
Figure 2:
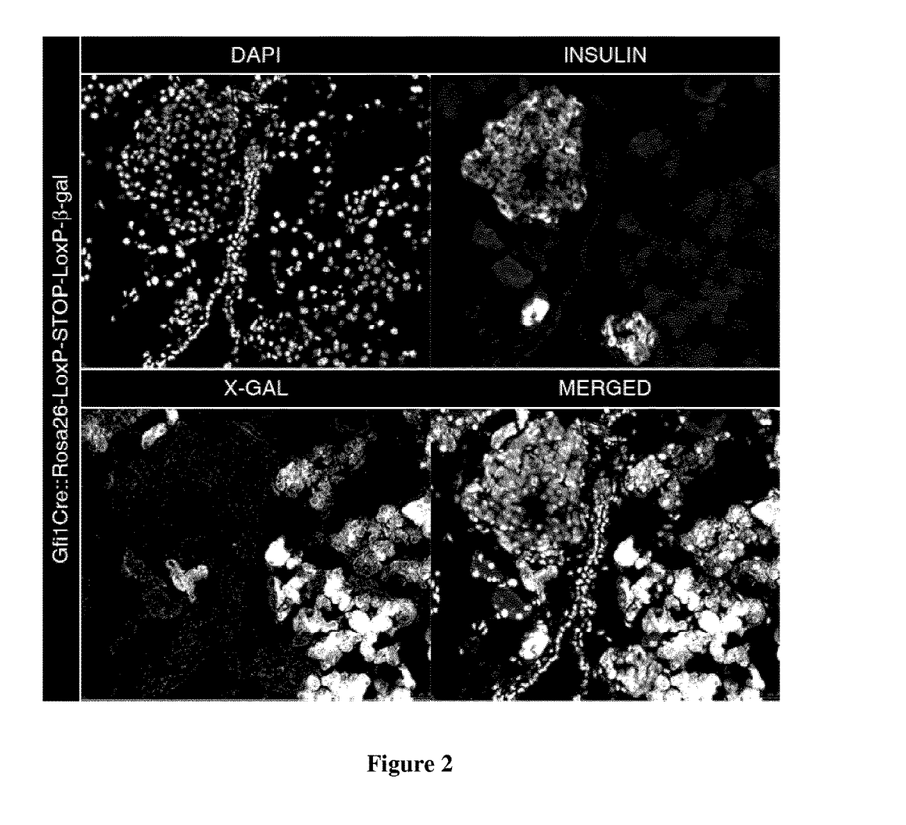
FIG. 2: X-gal staining and immunohistochemistry of Gfi1Cre::Rosa-lox--stop-lox-beta-Gal pancreas.

Through a thorough quantitative analysis using qRT-PCR, we demonstrated that Gfi1 is expressed in the pancreas, starting from the first stages of pancreatic embryonic development. Furthermore, we observed that Gfi1 mRNA levels remain steady throughout embryonic development, while they significantly increase during the first days of life (from Postnatal day 6). A further increase was also noted between 1 and 3 months of age. Afterwards Gfi1 expression appeared to be stable during adulthood until at least 12 months of life (FIG. 1). To investigate Gfi1 expression pattern, a Gfi1-Cre mouse line (expressing the phage P1 Cre Recombinase under the control of the endogenous Gfi1 promoter) was crossed with a ROSA26-β-gal mouse line (harboring a transgene containing the Rosa26 promoter upstream of a loxP-Neomycin resistance-Stop-loxP-β-galactosidase cassette). In the resulting Gfi1Cre::RosaLac animals, cells are permanently labelled once Gfi1 expression is activated. Thus, the spatiotemporal expression of β-galactosidase driven by Gfi1 promoter was analyzed by X-gal staining. β-galactosidase activity was solely detected in the acinar compartment. Importantly, no activity was found in ductal nor islets of Langerhans cells, demonstrating that the latter do not derive from cells having expressed Gfi1 (FIG. 2).

Gfi1 null animals suffer from several health conditions: loss of hearing, a general growth deficiency and severe neutropenia that impairs their life expectancy to a maximum of 1 month. To characterize the effects of Gfi1 ablation from the early phases of development to adulthood and thereafter, we therefore developed a conditional knock out system, where Gfi1 expression is silenced exclusively in the pancreas from the first phases of development. We thereby generated the Pdx1Cre::Gfi1cko transgenic mouse line (16). In the resulting animals, the Pdx1 promoter drives the expression of the Cre recombinase in all pancreatic cells. Once synthetized, the Cre recombinase induces Gfi1 loss-of-function solely in the pancreas. Pdx1Cre::Gfi1cko mice were found to be viable, fertile and to display a life expectancy comparable to that of control animals.

Figure 3:
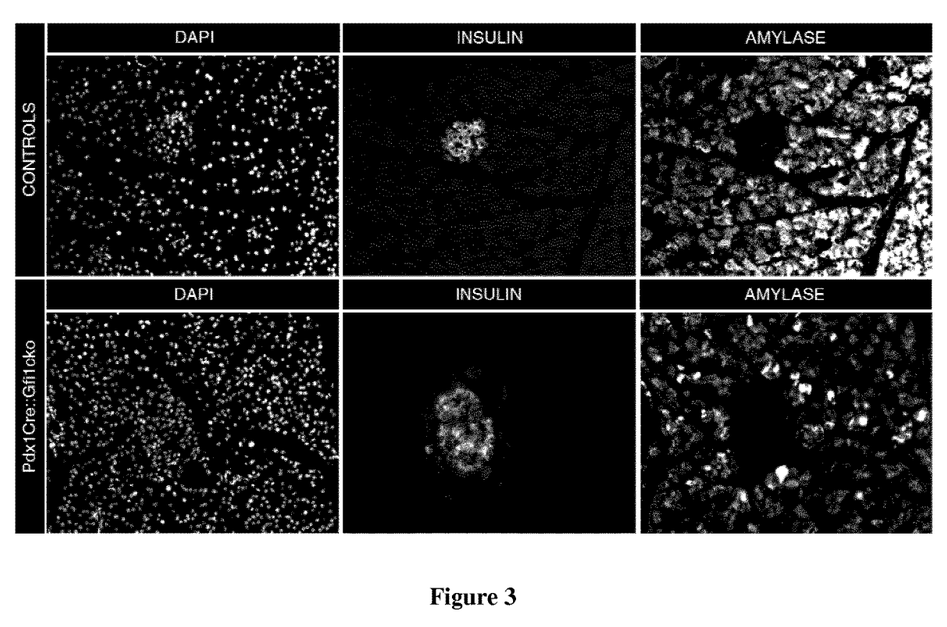
FIG. 3: Immunohistochemistry of adult pancreas labelled with insulin, amylase and DAPI.
Figure 4:
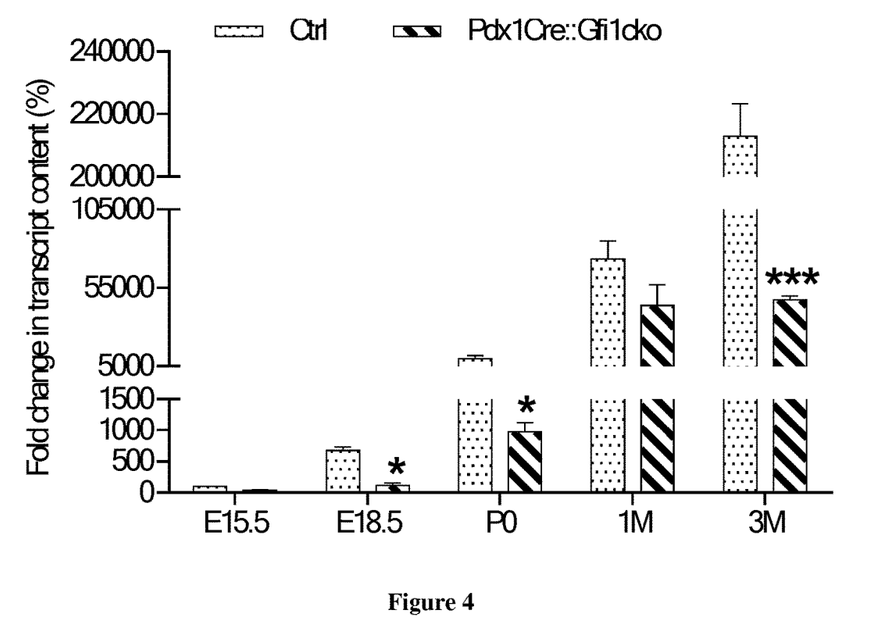
FIG. 4: qRT-PCR assessment of amylase gene expression from whole pancreas at different developmental and adult stages.

Pdx1Cre::Gfi1cko pancreata were thoroughly analyzed by immunohistochemistry. Our phenotypical characterization showed that the majority of acinar cells were either negative or weakly positive for amylase (FIG. 3). To confirm these observations, the amount of amylase transcript was assessed by RT-qPCR at different developmental and adult (st)ages. As expected, amylase expression levels increased significantly from E15.5 throughout postnatal life of control animals up to 3 months of age. Importantly, amylase transcript contents also raised continuously throughout pre- and postnatal development, but these were consistently decreased compared to controls at all ages tested. Strikingly, a significant 78.3% decrease in amylase expression level was measured in 3 months old Gfi1-mutants (FIG. 4).

Figure 5:
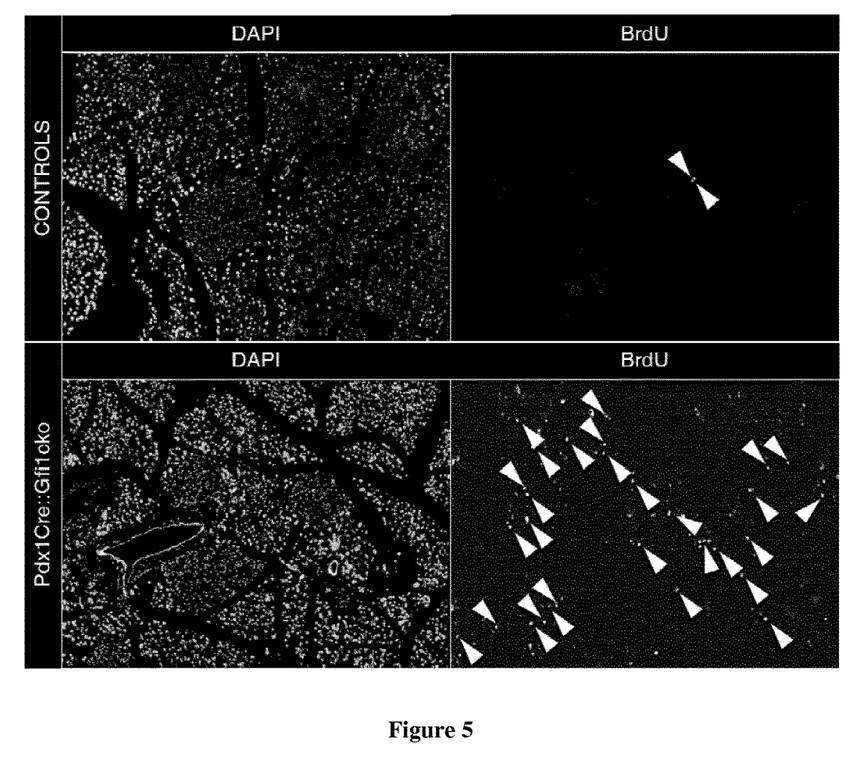
FIG. 5: Immunohistochemical assessment of BrdU-labelled cells.
Figure 6:
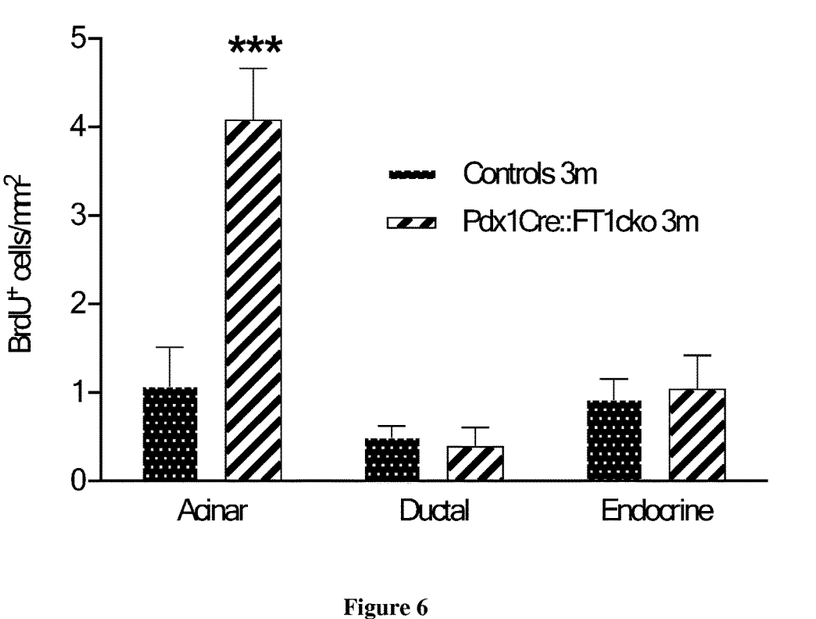
FIG. 6: Quantitative analyses of BrdU-labelled cells in different pancreatic compartments

Additionally, Gfi1 mutant acinar cells are hyperproliferative. Indeed, following 5 days of BrdU supplementation, BrdU immunoreactive cells were rarely observed in 3 months old control pancreata while an impressive number of dividing cells was detected in pancreatic sections isolated from adult Gfi1-deficient mice (FIG. 5). Quantitative analyses demonstrated that the increase in the cellular proliferation rate was restricted to the acinar compartment (FIG. 6).

Figure 7A:
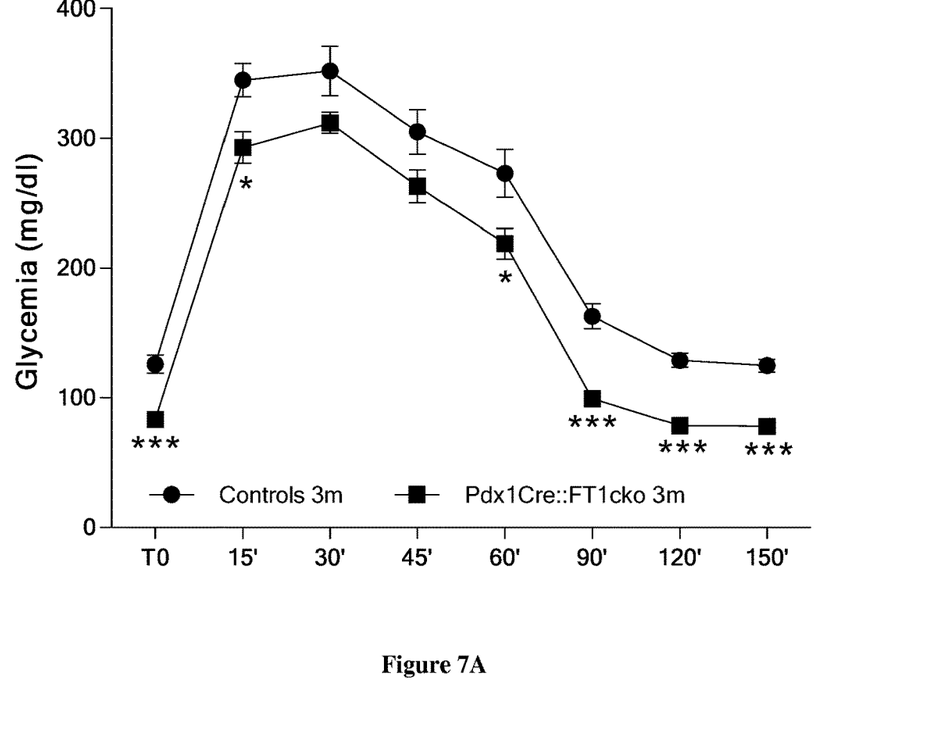
Figure 7B:
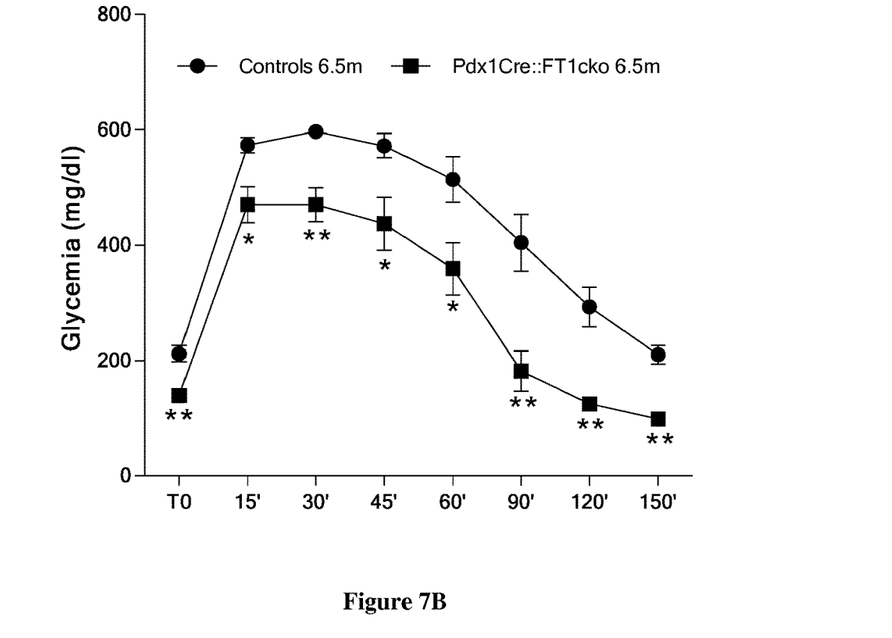
Figure 7C:
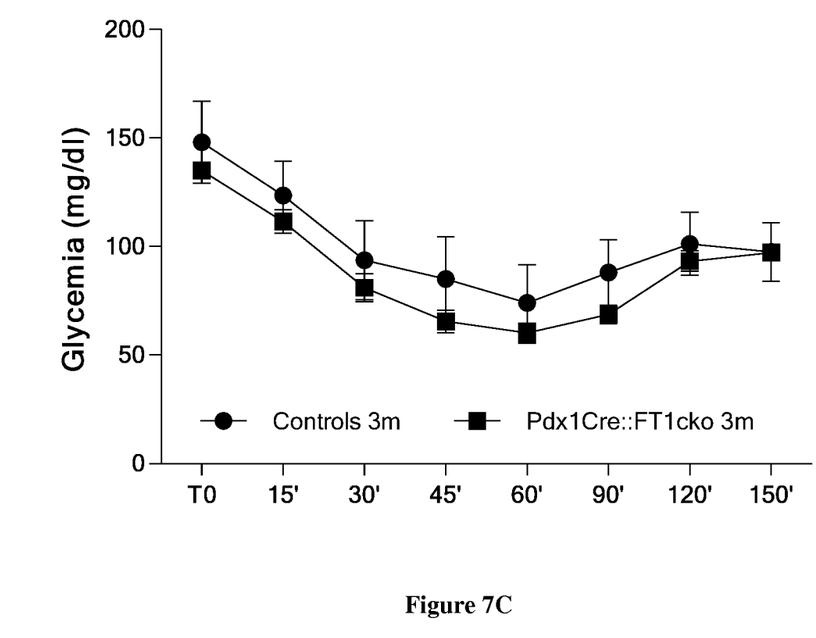
Figure 7D:
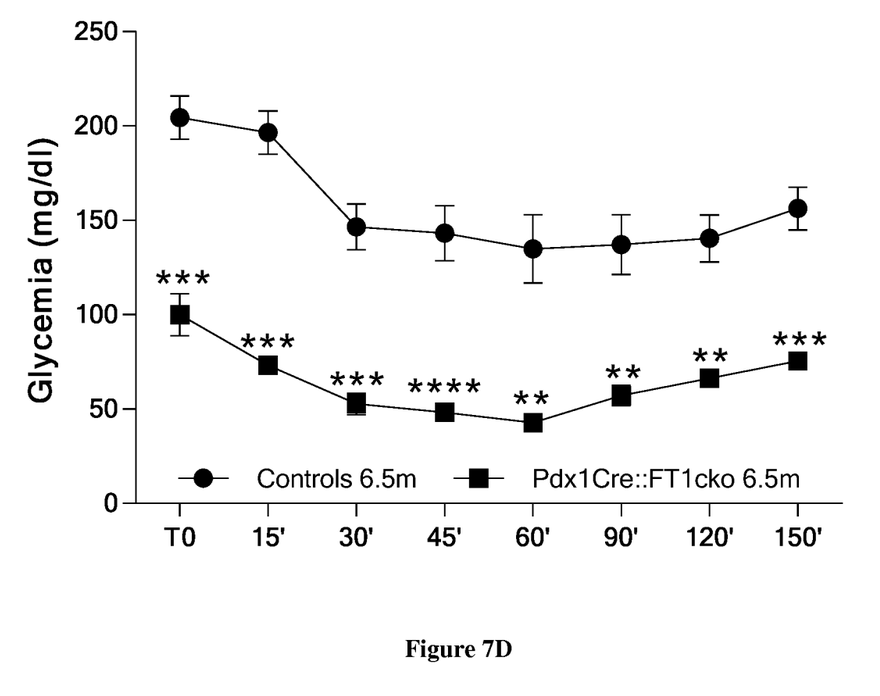
Figure 8A:
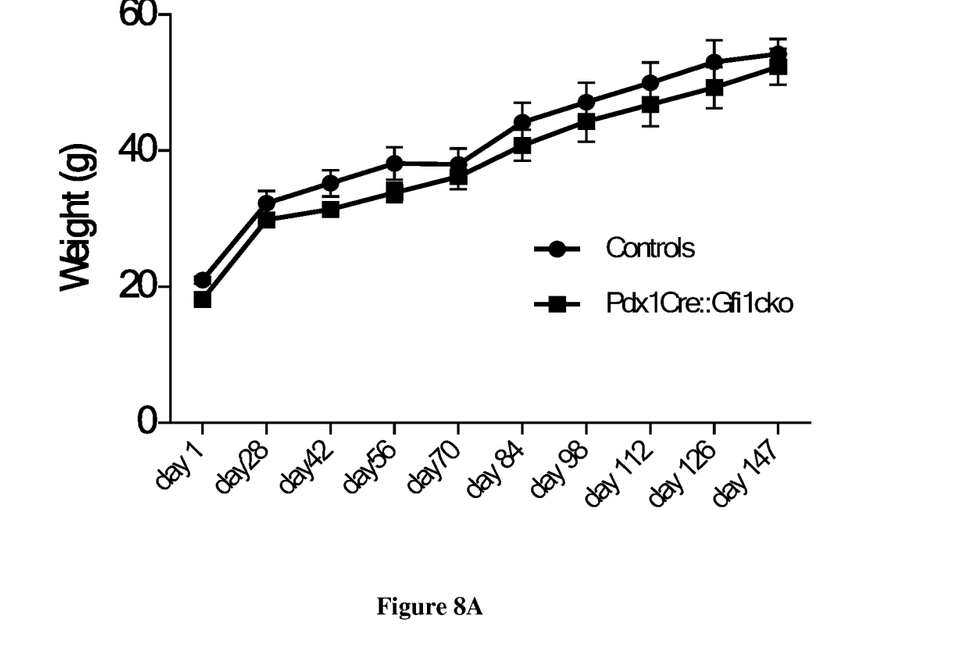
Figure 8B:
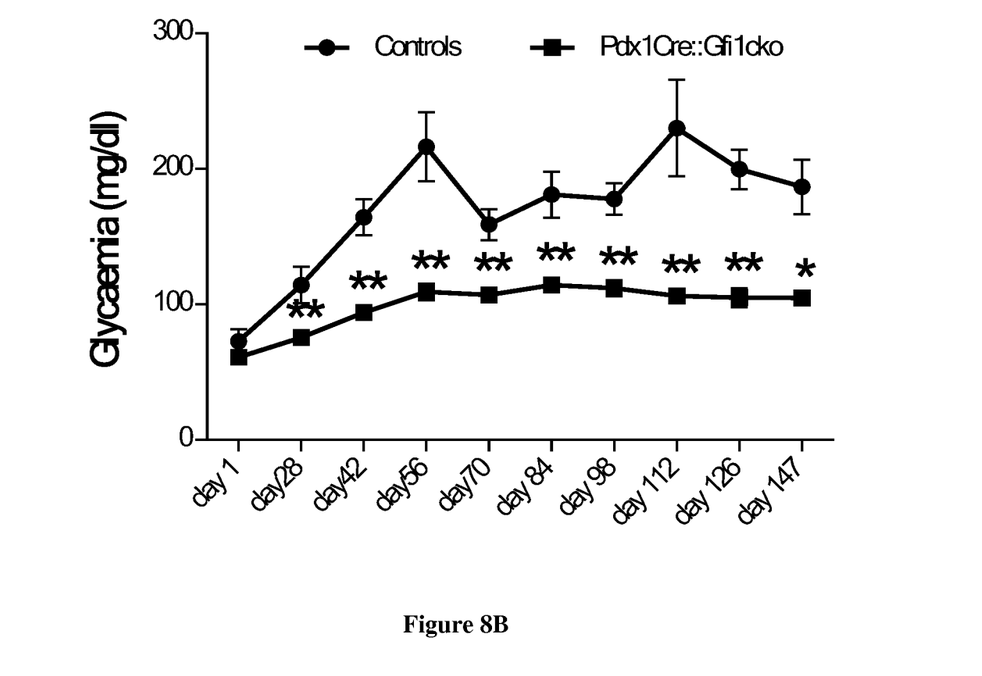
Figure 8C:
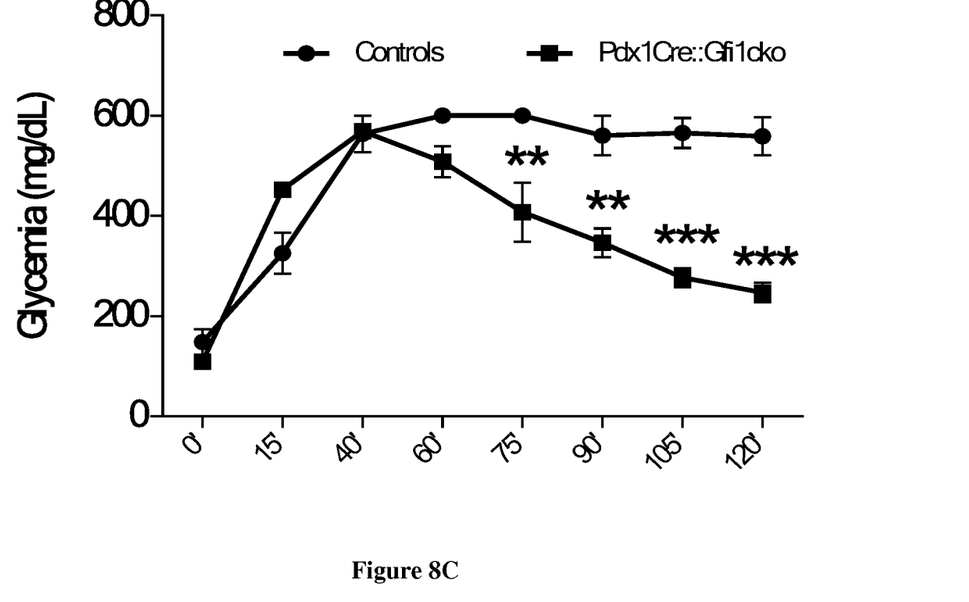
Figure 8D:
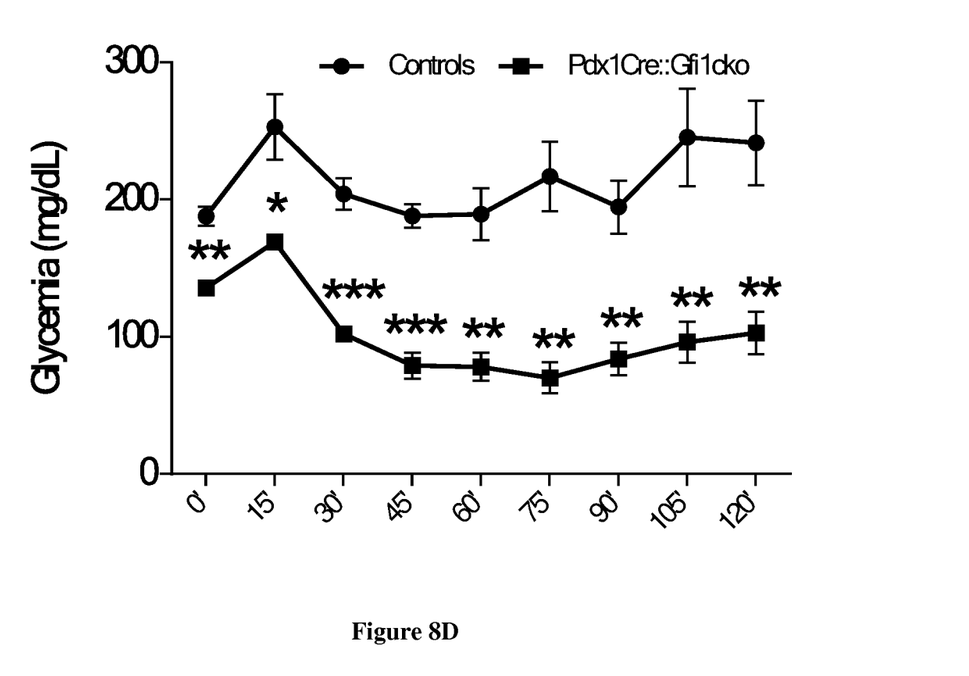

We extensively evaluated pancreas functionality, by performing several tests. We performed an intraperitoneal glucose tolerance test on 3-month old animals and noticed that the basal glycemia of Pdx1Cre::Gfi1cko was significantly lower, mutant mice displaying a better glucose tolerance compared to controls (FIG. 7A). However, no difference in insulin tolerance was found when we performed an intraperitoneal insulin tolerance test (FIG. 7C). Importantly, the differences in glucose handling were more dramatic when we compared 6-month old Pdx1Cre::Gfi1cko mice with age matched controls (FIG. 7B). Furthermore, at 6 months of age, Pdx1Cre::Gfi1cko mice were significantly more responsive to exogenous insulin administration compared to age matched controls (FIG. 7D). Importantly, we challenged Pdx1Cre::Gfi1cko mice with high fat diet (33.3% of anhydrous butter and 16.6% of sucrose—a known model of type 2 diabetes) for 5 months and monitored their weight and glycemia weekly. All the animals displayed a rapid increase in body mass as expected (FIG. 8A). Surprisingly, while control mice rapidly developed a massive hyperglycemia, mutant mice remained normoglycemic (with a glycemia lower than 120 mg/dl) throughout the entire experiment (FIG. 8B). At the end of the treatment, an intraperitoneal glucose tolerance test showed that Pdx1Cre::Gfi1cko mice were able to normally clear the blood of glucose in respect to the age-matched controls that showed an impaired capability (FIG. 8C). Lastly, an intraperitoneal insulin tolerance test demonstrated that Gfi1 mutant animals did not develop any insulin resistance upon high fat diet as seen for their control counterparts (FIG. 8D).

Figure 9:
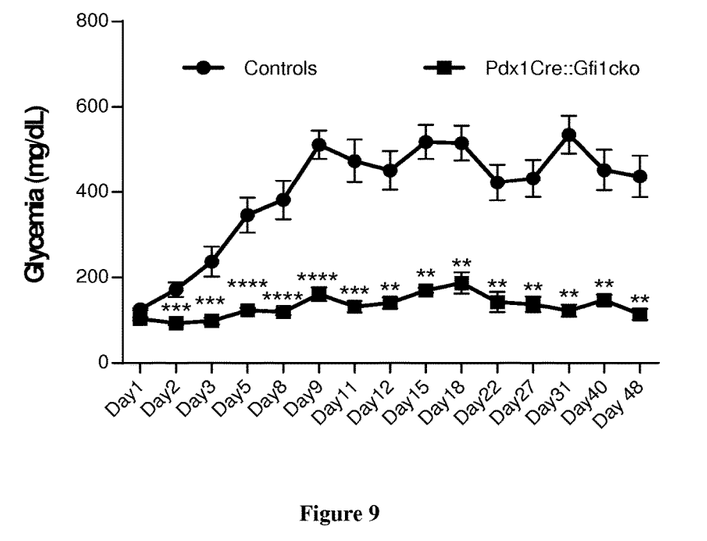
FIG. 9: Basal glycaemia monitoring of control and Gfi1 mutant mice treated with high dose streptozotocin. Arrow represent days of streptozotocin injection.
Figure 10:
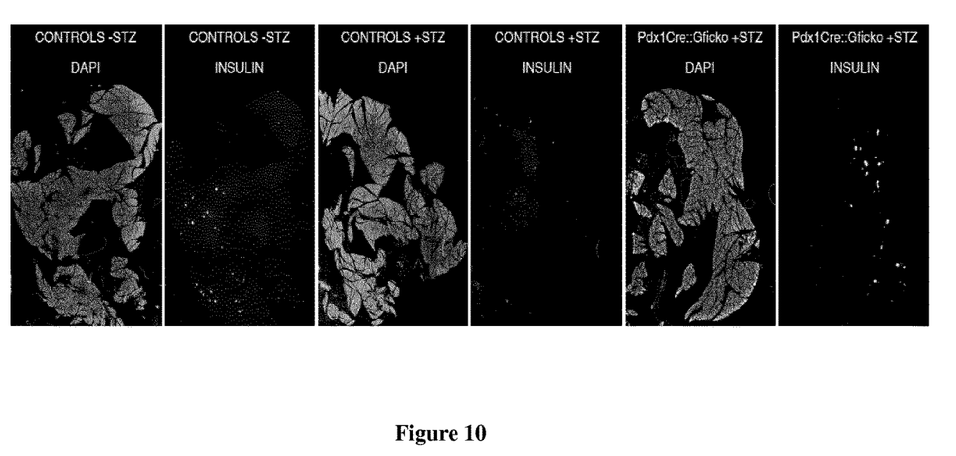
FIG. 10: Insulin immunostaining of pancreatic sections 5 days after acute streptozotocin treatment.

To determine whether Gfi1 loss could also be beneficial in Type I diabetes, we treated mutant and control mice with high dose streptozotocin to ablate their β-cells. Notably, 6 out of 9 controls responded to streptozotocin while all transgenic mice remained normoglycemic (FIG. 9). After 4 days, we re-injected Pdx1Cre::Gfi1cko and non-responsive control mice with high dose streptozotocin: while all control animals rapidly developed acute hyperglycemia, Pdx1Cre::Gfi1cko mice remained either normoglycemic or developed a temporary mild hyperglycemia from which they quickly recovered from (FIG. 9). In a subsequent experiment, mice were sacrificed 5 days after streptozotocin injection and pancreas specimens were analyzed by immunohistochemistry. Surprisingly, the β-cell mass and islets of Langerhans integrity were found unaffected by streptozotocin cytotoxic activity in Gfi1 conditional knockout pancreata (FIG. 10).

Figure 11:
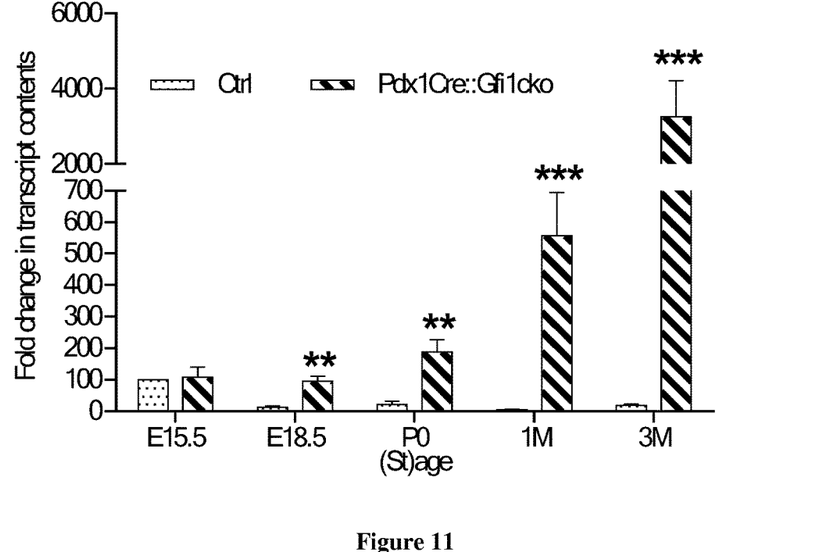
FIG. 11: qRT-PCR quantification of NKX6.2 mRNA levels from whole pancreas at different developmental and adult stages.
Figure 12:
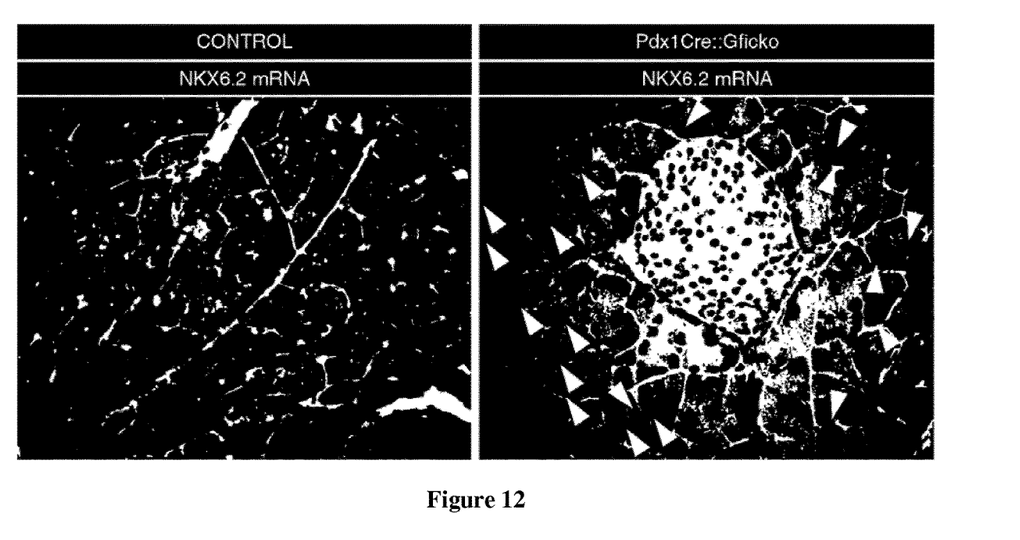
FIG. 12: RNA scope targeting NKX6.2 mRNA

To dissect the molecular pathway underlying Gfi1 activities in the pancreas, we analyzed the pancreatic transcriptome extracted from Gfi1-deficient mice by RT-qPCR and assessed the expression level of all genes known for their involvement in pancreas development and function. Using this approach, we found that Nkx6.2 was abnormally expressed in Pdx1Cre::Gfi1cko mice. Nkx6.2 transcripts were solely detected at E15.5 in control pancreas, Nkx6.2 being subsequently switched off (FIG. 11). Importantly, Pdx1Cre::Gfi1cko pancreatic cells failed to inactivate Nkx6.2 expression during the latest stages of embryonic development (FIG. 11). Interestingly, by means of RNA scope, we detected Nkx6.2 mRNA molecules exclusively in the acinar cells (FIG. 12), suggesting a role of Nkx6.2 reactivation in the phenotype exhibited by Pdx1Cre::Gfi1cko mice. Together, our results indicate that the loss of Gfi1 in the pancreas results in a protection from all models of diabetes. Such protection originates in the acinar pancreas with appears altered with the loss of amylase, an hyperproliferation and a misexpression of Nkx6.2. All these evidence point to an altered absorption of glucose and role of Gfi1 in controlling beta-cell function.

REFERENCES

Throughout this application, various references describe the state of the art to which this invention pertains. The disclosures of these references are hereby incorporated by reference into the present disclosure.

1. Slack J M. Developmental biology of the pancreas. Development. 1995 June; 121(6):1569-80. PubMed PMID: 7600975.
2. Konstantinova I, Nikolova G, Ohara-Imaizumi M, Meda P, Kucera T, Zarbalis K, et al. EphA-Ephrin-A-mediated beta cell communication regulates insulin secretion from pancreatic islets. Cell. 2007 Apr. 20; 129(2):359-70.
3. Prado C L, Pugh-Bernard A E, Elghazi L, Sosa-Pineda B, Sussel L. Ghrelin cells replace insulin-producing beta cells in two mouse models of pancreas development. Proceedings of the National Academy of Sciences of the United States of America. 2004 Mar. 2; 101(9):2924-9.
4. Adrian T E, Bloom S R, Hermansen K, Iversen J. Pancreatic polypeptide, glucagon and insulin secretion from the isolated perfused canine pancreas. Diabetologia. 1978; 14(6):413-7.
5. Csaba Z, Dournaud P. Cellular biology of somatostatin receptors. Neuropeptides. 2001; 35(1):1-23.
6. Roncoroni L, Violi V, Montanari M, Muri M. Effect of somatostatin on exocrine pancreas evaluated on a total external pancreatic fistula of neoplastic origin. Am J Gastroenterol. 1983; 78(7):425-8.
7. Heller R S, Jenny M, Collombat P, Mansouri A, Tomasetto C, Madsen O D, et al. Genetic determinants of pancreatic epsilon-cell development. Developmental biology. 2005 Oct. 1; 286(1):217-24.
8. Vignjevic S, Todorovic V, Damjanovic S, Budec M, Mitrovic O, Djikic D, et al. Similar developmental patterns of ghrelin- and glucagon-expressing cells in the human pancreas. Cells, tissues, organs. 2012; 196(4):362-73. PubMed PMID: 22538872.
9. Wierup N, Svensson H, Mulder H, Sundler F. The ghrelin cell: a novel developmentally regulated islet cell in the human pancreas. Regulatory peptides. 2002 Jul. 15; 107 (1-3):63-9. PubMed PMID: 12137967.

10. Shih H P, Wang A, Sander M. Pancreas organogenesis: from lineage determination to morphogenesis. Annu Rev Cell Dev Biol. 2013; 29:81-105. PubMed PMID: 23909279.
11. Arda H E, Benitez C M, Kim S K. Gene regulatory networks governing pancreas development. Developmental cell. 2013 Apr. 15; 25(1):5-13. PubMed PMID: 23597482. Pubmed Central PMCID: 3645877.
12. Hock H, Orkin S H. Zinc-finger transcription factor Gfi-1: versatile regulator of lymphocytes, neutrophils and hematopoietic stem cells. Current opinion in hematology. 2006 January; 13(1):1-6. PubMed PMID: 16319680.
13. Linnoila R I, Jensen-Taubman S, Kazanjian A, Grimes H L. Loss of GFI1 impairs pulmonary neuroendorine cell proliferation, but the neuroendocrine phenotype has limited impact on post-naphthalene airway repair. Laboratory investigation; a journal of technical methods and pathology. 2007 April; 87(4):336-44. PubMed PMID: 17377622. Pubmed Central PMCID: 2839158.
14. Shroyer N F, Wallis D, Venken K J, Bellen H J, Zoghbi H Y. Gfi1 functions downstream of Math1 to control intestinal secretory cell subtype allocation and differentiation. Genes & development. 2005 Oct. 15; 19(20): 2412-7. PubMed PMID: 16230531. Pubmed Central PMCID: 1257395.
15. Wallis D, Hamblen M, Zhou Y, Venken K J, Schumacher A, Grimes H L, et al. The zinc finger transcription factor Gfi1, implicated in lymphomagenesis, is required for inner ear hair cell differentiation and survival. Development. 2003 January; 130(1):221-32. PubMed PMID: 12441305.
16. Gannon M, Herrera P L, Wright C V. Mosaic Cre-mediated recombination in pancreas using the pdx-1 enhancer/promoter. Genesis. 2000 February; 26(2):143-4. PubMed PMID: 10686611.
17. Zhu J, Jankovic D, Grinberg A, Guo L, Paul W E. Gfi-1 plays an important role in IL-2-mediated Th2 cell expansion. Proceedings of the National Academy of Sciences of the United States of America. 2006 Nov. 28; 103(48): 18214-9. PubMed PMID: 17116877. Pubmed Central PMCID: 1654136.

The invention claimed is:

1. A method of treating hyperglycemia in a subject in need thereof, comprising administering to the subject a therapeutically effective amount of an inhibitor of growth factor independent 1 transcriptional repressor (Gfi1/Gfi1A), wherein the inhibitor is a siRNA comprising an antisense strand with sufficient complementarity to Gfi1 mRNA to inhibit its expression.

* * * * *